United States Patent [19]

Yokobayashi et al.

[11] 4,306,059

[45] Dec. 15, 1981

[54] SHAPED PRODUCTS OF ALPHA-GLUCAN

[75] Inventors: Koji Yokobayashi; Toshiyuki Sugimoto, both of Okayama, Japan

[73] Assignee: Kabushiki Kaisha Hayashibara Seibutsu Kagaku Kenkyujo, Okayama, Japan

[21] Appl. No.: 945,129

[22] Filed: Sep. 25, 1978

[30] Foreign Application Priority Data

Sep. 30, 1977 [JP] Japan ................. 52-117667

[51] Int. Cl.$^3$ ............................. C07G 37/00
[52] U.S. Cl. ......................... 536/1; 71/11; 106/139; 106/162; 106/213; 131/352; 131/355; 252/9; 252/352; 424/180; 426/104; 426/573; 264/186
[58] Field of Search ............................ 536/1

[56] References Cited

U.S. PATENT DOCUMENTS

| | | | |
|---|---|---|---|
| 3,228,928 | 1/1966 | Opie et al. | 536/114 |
| 3,297,604 | 1/1967 | Germino | 536/114 |
| 3,784,390 | 1/1974 | Hijiya et al. | 106/139 |
| 3,870,537 | 3/1975 | Hijiya et al. | 536/1 |
| 3,899,480 | 8/1975 | Kimura et al. | 536/1 |
| 4,018,233 | 4/1977 | Miyake | 536/1 |
| 4,072,567 | 2/1978 | Yokobayashi et al. | 536/1 |

OTHER PUBLICATIONS

Tsumuraya et al., "Chem. Abst.", vol. 89, 1978, p. 192778s.

*Primary Examiner*—Johnnie R. Brown
*Attorney, Agent, or Firm*—Browdy and Neimark

[57] ABSTRACT

Products such as film, sheet, paper, fiber, coating material, binder, and molded materials e.g. capsules, cups et al are disclosed. The products are prepared by use of an alpha-glucan comprising repeating units of [3)-Glc-(1→4)-Glc-(1→4)-Glc-(1→], (wherein Glc represents alpha-D-glucopyranose residue) as its sole constituent or a member of its constituents according to conventional methods.

4 Claims, 2 Drawing Figures

SHAPED PRODUCTS OF ALPHA-GLUCAN

DETAILED DESCRIPTION OF THE INVENTION

The invention relates to shaped products prepared by use of a novel alpha-glucan (Elsinan) comprising repeating units of [3)-Glc-(1→4)-Glc-(1→4)-Glc-(1→], (wherein Glc represents alpha-D-glucopyranose residue, hereinafter referred to as Glc).

Conventionally, alpha-glucans such as amylose and pullulan have been used for making shaped bodies.

When amylose is used for making shaped bodies, for example, film, it is necessary to pregelatinize the amylose by heating to a high temperature, 130° to 150° C. Even in a film prepared with the gelatinized amylose the amylose retrogrades and forms a crystal structure, and the film becomes opaque and increases its brittleness. Therefore a film with satisfactory transparency, toughness and stability could not be prepared with amylose.

Unlike shaped bodies prepared with amylose, those prepared with pullulan are stable, effecting no retrogradation but have the disadvantages of being susceptible to water.

The inventors performed painstaking research and development to eliminate the disadvantages of these alpha-glucans. The efforts resulted in the discovery of a novel alpha-glucan (Elsinan) and the finding that the alpha-glucan provides shaped bodies which are moisture resistant, water resistant, hot water soluble, transparent, non-toxic, edible, and, moreover, storable for prolonged periods without losing their desirable properties.

More particularly, the novel alpha-glucan used in the invention is an alpha-glucan that is separated and recovered from a highly viscous culture broth obtained by inoculating a microorganism of genus Elsinoe on a nutrient medium containing one or more sugars such as sucrose, glucose, maltose, fructose and starch hydrolysates, and incubating the inoculated medium at a temperature from 20° to 30° C. for 3 to 7 days. The inventors designated the novel glucan as elsinan.

The elsinan was identified as alpha-glucan, based on the following properties.

Purity: No contaminants were detectable on subjection to ultracentrifugation and electrophoresis.

Element analysis: Measurements; C=43.7%, H=6.16%, N<0.1%, Ash<0.01%, Calculations; C=44.4%, H=6.17%

Specific rotation: $[\alpha]_D^{25}$ +175°~280° (l=1, c=1.6, 0.5 N-NaOH)

Solubility: Dissolves readily in water, 0.1 N-NaOH, 90% formic acid, formamide, or dimethyl sulfoxide. Insoluble in organic solvents such as methanol, ethanol, acetone, chloroform or ethyl acetate.

Appearance: A white, fine powder without taste or odor.

Color reactions: Becomes green by the anthrone-sulfuric reaction. Becomes yellow by the cystein-sulfuric acid reaction. Remains colorless by the Morgan-Elson reaction. Iodine stain, negative.

Figure 1:
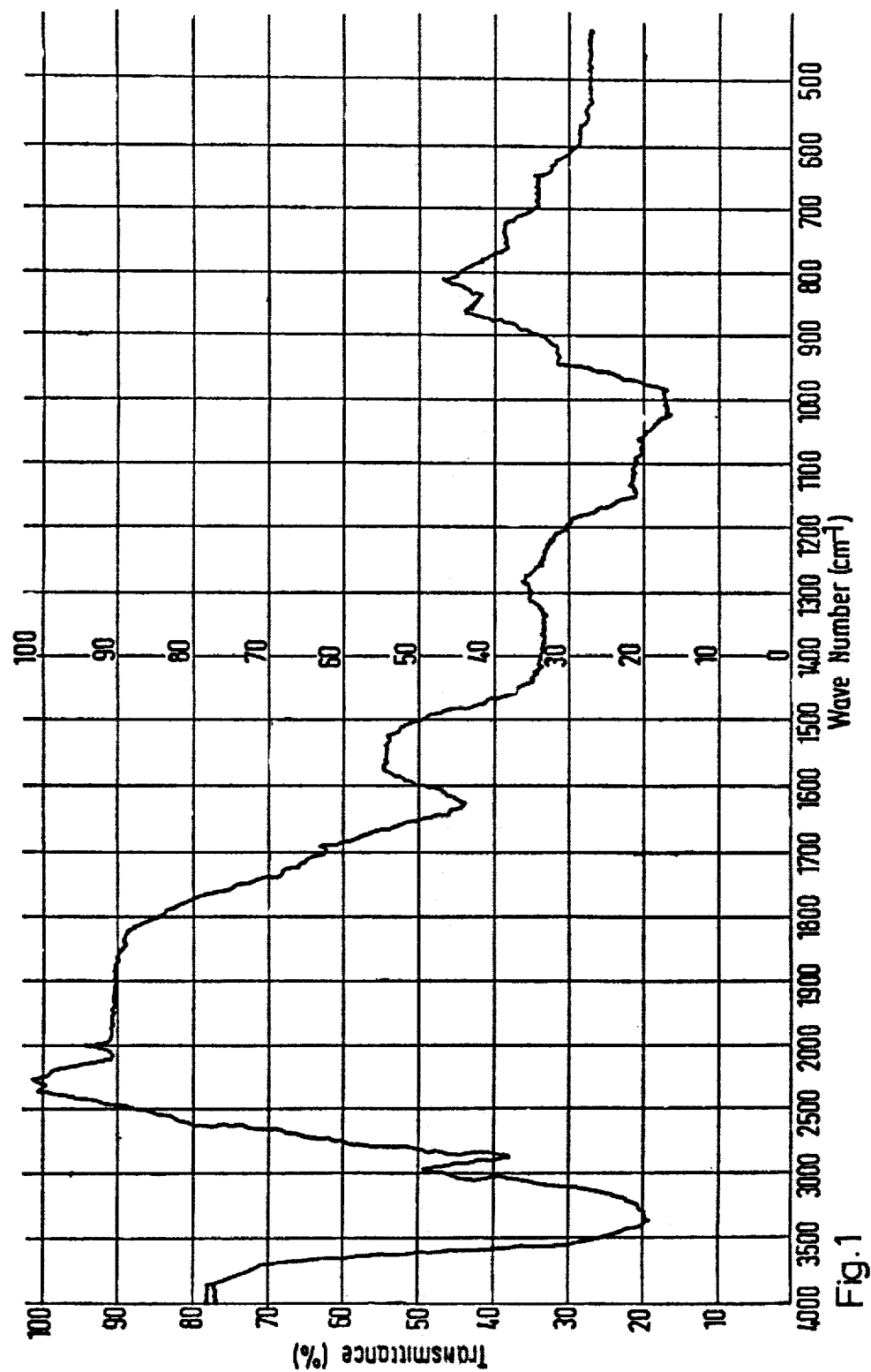

Infrared spectrum: Infrared spectrum by the KBr tablet is given in FIG. 1. The absorbance at 840 cm$^{-1}$ in the infrared spectrum was characteristic of the alpha-type linkage.

Components: The analytical results obtained by paper chromatography, gas chromatography, liquid chromatography and glucose oxidase peroxidase method showed that the sugar obtained from hydrolyzing elsinan with 1 N-sulfuric acid, 1 N-hydrochloric acid or 1 N-trichloroacetic acid was D-glucose.

In addition, the analytical results obtained by using chemical procedures such as methylation, periodate oxidation, Smith degradation and controlled Smith degradation show that the elsinan disclosed in the present invention is a novel glucan with an entirely new structure so far unkown. The novel glucan (Elsinan) will be disclosed in further details.

(1) The high specific rotation, $[\alpha]_D^{25}$ +175°~280°, and the absorbance at 840 cm$^{-1}$ in the infrared spectrum indicate that all or most of the glucosidic linkages constructing elsinan are of alpha type.

(2)

a. Qualitative and quantative analyses by gas chromatography and mass spectrum of the hydrolysate of methylated elsinan show that the major components are 2,4,6-tri-0-methyl-D-glucose (ca. 30%) and 2,3,6-tri-0-methyl-D-glucose (ca. 68%), with small amounts of 2,4-di-O-methyl-D-glucose (ca. 1%) and 2,3,4,6-tetra-O-methyl-D-glucose (ca. 1%) present.

b. Complete oxidation of elsinan with periodate shows that 0.8 moles of periodate is consumed per glucose residue, with simultaneous formation of 0.07 moles of formic acid per glucose residue.

c. Qualitative and quantative analyses by paper chromatography, gas chromatography and liquid chromatography of the Smith degradation products of elsinan confirm that D-erythritol, 68~70%; D-glucose, 29~30%; glycerol, a trace.

The above results confirm that the glucose residues present in elsinan are essentially linear molecules comprising mainly alpha-1,4 and alpha-1,3 linkages in the molar ratio of 2.0~2.3:1.0.

A very few of the glucose residues linked at the C-1 and C-3 positions with the adjacent glucose residues are branched at the C-6 position by alpha-1,6 linkage. Such glucose residues are, at most, one out of every 70 glucose residues.

(3) The analyses by paper chromatography and gas chromatography of controlled Smith degradation products of elsinan indicate that D-erythritol and 2-O-alpha-D-glucopyranosyl-D-erythritol are present in the molar ratio of 1.0~1.3:1.0 (the presence of 2-O-alpha-D-glucopyranosyl-D-erythritol indicates that the glucose residue is linked at the C-3 position by alpha-1,3-linkage with one adjacent glucose residue, and linked at the C-1 position by alpha-1,4 linkage with the adjacent glucose residue on the other side). In addition, a trace amount of glycerol derived from the non-reducing terminal glucose residue is detected.

(4) Partial hydrolysis of elsinan with dilute acid demonstrates that maltotriose, a small amount of maltotetraose, and other trisaccharides and tetra-saccharides containing both alpha-1,4 and alpha-1,3 linkages are present in the hydrolysate.

The above observations, (1), (2), (3) and (4), show that the elsinan disclosed in the invention is a polysaccharide which is hardly branched and which comprises alpha-1,3 and alpha-1,4 linkages, with the main structure in which approx. three alpha-1,4 linked-glucose residues are repeatedly linked in alpha-1,3 fashion. In other words, the elsinan has an essentially linear-chain structure wherein maltotriose units are linked repeatedly in alpha-1,3 fashion. The observations, (2), (3) and (4), also show that, although repeating units are predominantly maltotriose, maltotetraose residue is present in a small amount.

Consequently, elsinan is a novel glucan comprising repeating units of [3)-Glc-(1→4)-Glc-(1→4)-Glc-(1→].

The structure of elsinan can be illustrated as below.

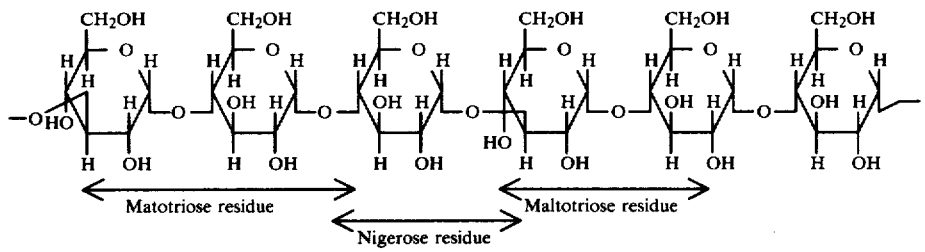

The mean molecular weight of elsinan is freely adjustable in the range of approx. 5,000 to approx. 10,000,000, because the glucan is producible by either chemical or biochemical procedure and is easily hydrolyzable with hydrochloric acid, sulfuric acid, etc.

The present invention is based on the discovery by the inventors that elsinan is a material from which various shaped bodies such as granule, pellet, filament, fiber, thread, stick, rod, rope, net, cloth, gauze, film, sheet, paper, tube, capsule, tablet, sponge, laminate and coating can be formed freely and easily by commonly known methods.

For making shaped bodies any form or phase of elsinan is employable as material; in powder, paste or liquid.

As described above, although the average molecular weight of elsinan is freely controllable, the suitable range for material to prepare shaped bodies is 10,000 to 10,000,000.

For shaping the bodies, the temperature should be lower than 250° C., the point that effects carbonization of elsinan, and the pH in the stable pH range for elsinan, 2 to 11.

The shaping method can be freely selected, according to the use, from known methods, for example, compression molding, transfer molding, laminate molding, injection molding, extrusion molding, blow molding, calendering, vacuum forming and coating.

The shaping is carried out, generally, under a pressure in the range from 0 to 1,000 kg/cm$^2$.

In the production of shaped bodies of the invention, elsinan can be used alone, or also used freely in combination with one or more members selected from the group comprising plasticizer, filler, excipient, thickener, adhesive, foaming agent, flame retarder, surface lubricant, antimicrobial agent, coloring agent, nutrient, flavor, physiologically active substance, medicinal substance, and condiment.

Employable plasticizers are, for example, glycerol, ethylene glycol, polyethylene glycol, propylene glycol, polyvinyl alcohol, sorbitol, mannitol, xylitol, maltitol, dimethylsulfoxide, and dimethyl formamide.

Employable fillers or excipients are organic matters, for example, carbohydrate such as starch, wheat flour, carboxymethylcellulose, pullulan, amylose, cellulose, pulp, wood flour, pectin, gum arabic, alginate, glucose, maltose, sucrose, lactose and starch hydrolysates, protein such as casein, gluten and gelatin, thermosetting resin such as phenol resin and melamine resin, thermoplastic resin such as vinyl chloride resin and polystyrene, and inorganic matters, for example, silica sand, borax, volcanic ash, diatomaceous earth, bentonite, alumina, carbon black, calcium carbonate, glass fiber, and metal fiber.

The mixing ratio of elsinan to other materials should be in the range of 0.0001 to 10,000, preferably, 0.001 to 1,000 based on dry weight.

The shaped bodies of the invention can be used, for example, as consumption goods for food, clothing, house, building and industries for many applications as well as agriculture, forestry, fisheries, and stock raising, and also as industrial materials for chemical, cosmetic and pharmaceutical.

The main features of an elsinan film will be exemplified as those for the shaped bodies prepared in accordance with the invention.

(1) Water soluble, highly moisture-and water-resistant, and non-blocking

The film is easily soluble in hot water with a temperature of about 80° C. and above. In water of a temperature below about 40° C., it only swells but maintains its initial shape. No blocking phenomena are noted under highly humidic- or wet-conditions at room temperature.

(2) Desirably stretchable

The elongation percentage can be freely changed by varying the type and the amount of plasticizer such as water and glycerin. If necessary, the film can be prepared by casting and winding.

(3) Stable to retrogradation

The desirable initial properties, transparency, flexibility and folding endurance of the film, can be maintained for a long period because the film does not retrograde. Since the film is hardly affected by variation in humidity and by the addition or non-addition of plasticizer, it is more excellent than those prepared with amylose or pullulan.

(4) Heat-sealable

Even though the elsinan film is low in moisture content, below 20 w/w %, it can be easily and firmly heat-sealed.

(5) Tough and flexible

The elsinan film is extremely tough and flexible, and the properties are superior to those of any other alpha-glucan film.

(6) Oil resistant

The film has high resistances to fats, oils, oily foods and oil soluble vitamin.

(7) Gas impermeable

The film is high in gas impermeability since its oxygen-or air-permeability is extremely low. In other words, elsinan can act as an oxidation barrier for easily oxidizable products by atmospheric oxygen, for example, foods such as perishable foods, oily foods, processed foods, pharmaceuticals such as vitamin, enzyme, hormone and biomedicals, and other materials such as botanical seeds and metals, when it is used as film to seal, package or wrap the products, or to apply a coating thereon. The film or coating is highly effective in retaining the original flavors of the contents because volatilization of flavor ingredients can be prevented.

(8) Non-conductive and electric chargeable

The film can be used as an insulator for electric machinery and tools.

(9) Glossy, colorless, transparent, tasteless, odorless, edible and non-toxic

If necessary, the film can be freely colored, made opaque, seasoned, and flavored. Elsinan is a polysaccharide whose constitutive sugar is alpha-D-glucopyranose. The acute toxicity tests with orally administrating elsinan to rats showed an extremely low toxicity, not less than 25 g/kg for $LD_{50}$.

(10) Hydrolizable by alpha-amylase

The film is decomposed readily by alpha-amylase in the digestive tract. Various medicines can be orally administered to display their efficacy at the proper time and site and for desirable period in digestive tract by sealing, tableting or encapsulating the medicines in elsinan shaped bodies of adequate shape, structure or composition.

(11) Non-environmental pollutant

The film distinguishes itself from conventional petrochemical plastics in that it generates no high heat, soot, tar, and poisonous gases that damage incinerators, and in that it has no fear of causing of atmospheric pollution. Even if it is dumped in river or sea, there is no fear of environmental pollution because it is readily biodegradable.

As described above, shaped bodies using elsinan have many excellent characteristics.

The following experiments exemplify production of elsinan.

Experiment 1

A liquid medium consisting of 5 w/v % sucrose, 0.5 w/v % yeast extract, 0.042 w/v % $Na_2HPO_4$, 0.018 w/v % $KH_2PO_4$, semi-permeable-membrane-permeated solution of potato extract with hot water (300 g fresh potato was used per one liter medium.) and water was sterilized at 120° C. for 20 minutes, and then cooled. Thereafter, the medium was inoculated with *Elsinoe leucospila*, FERM-P No. 3874, at an initial pH of 6.8, and subjected to submerged culture at 24° C. for five days. After pasteurizing the resultant broth at 85° C. for 15 minutes, the cells and mycelia were removed therefrom by centrifugation (5,000 g for 20 minutes). With the addition of 1.5 volumes ethanol to the thus-obtained clear supernatant, crude elsinan was obtained as a precipitate in a plumage or gum form. The crude elsinan was dissolved in water and subjected to centrifugation to remove insoluble substances, as described above, and then precipitation was effected by adding ethanol again to the supernatant. After the procedure was repeated three times, the precipitate was lyophilized. White powder of purified elsinan was obtained at an approx. 30% yield against the sucrose used in the medium.

Figure 2:
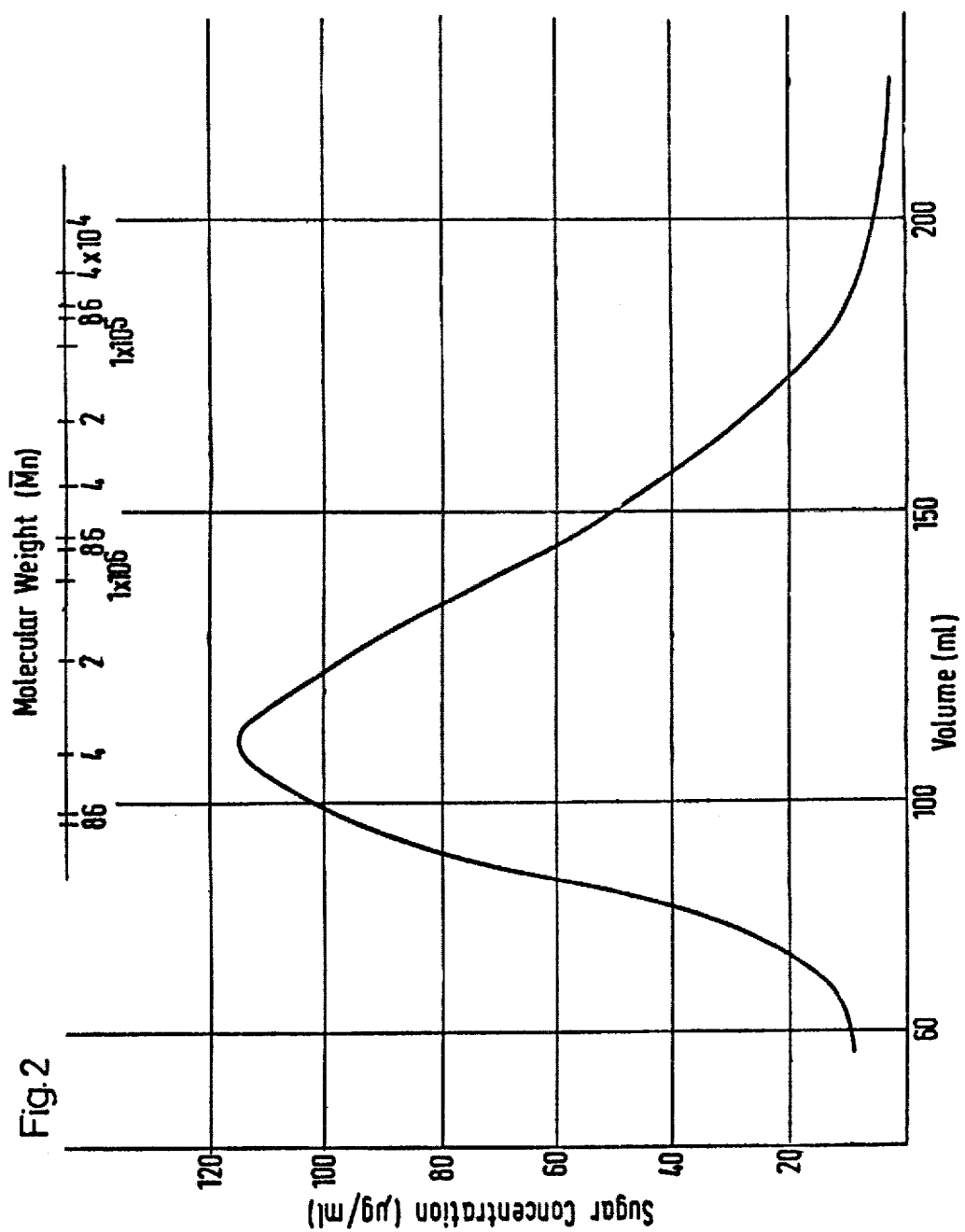

The viscosity of a 3 w/w % aqueous solution of the purified elsinan determined at 30° C., using Brookfield rotational viscometer, was 407 cps. The estimation of molecular weight distribution of the purified elsinan by the gel filtration method gave a distribution range from approx. 10,000 to approx. 10,000,000 or more, as illustrated in FIG. 2.

Experiment 2

A liquid medium, consisting of 3 w/v % partial starch hydrolysate (starch syrup solid with a DE of 30), 0.3 w/v % wheat germ, 0.1 w/v % $NH_4NO_3$, 0.1 w/v % $K_2HPO_4$, 0.05 w/v % $MgSO_4.7H_2O$, 0.05 w/v % KCl, 0.0001 w/v % $MnSO_4.4H_2O$ and water, was sterilized at 120° C. for 20 minutes and then cooled. Thereafter, the medium was inoculated with *Elsinoe fawcetti* IFO 8417 at an initial pH of 6.0 and subjected to submerged culture at 28° C. for four days.

The resultant cultural broth was treated similarly as described in Example 1, and purified elsinan (white powder) was obtained at an approx. 70% (d.s.b.) yield against the partial starch hydrolyzate used in the medium.

The thus obtained elsinan can be freely used for making various shaped bodies as shown in the following examples.

EXAMPLE 1

Film

Five w/w % aqueous elsinan solutions containing 0, 5, or 10 w/w % glycerin based on elsinan against dry matter (hereinafter referred to as d.s.b.) were prepared and cast on glass plates, and then the plates were dried with hot air at 70° C. to obtain a transparent, tough and flexible film.

Films used as controls were prepared in a similar manner as described above except that pullulan or amylose was used instead of elsinan. After storing the obtained films for 3 months under the conditions of relative humidities (hereinafter abbreviated to as RH) of 33, 65 and 90% at 25° C., the water contents (equilibrium moisture content) of the films were measured and the properties of the films were tested.

The results are shown in Table 1.

TABLE 1

| Film material | Glycerine added(%) | RH 33% water content | RH 33% properties | RH 65% water content | RH 65% properties | RH 90% water content | RH 90% properties |
|---|---|---|---|---|---|---|---|
| Elsinan (the product of the invention) | 0 | 11.1 | O | 15.2 | O | 19.5 | O |
| | 5 | 12.4 | O | 15.5 | O | 20.3 | O |
| | 10 | 12.6 | O | 15.5 | O | 20.5 | O |
| Pullulan (control) | 0 | 10.0 | O | 13.0 | O | 21.1 | x |
| | 5 | 10.3 | O | 14.1 | O | 22.1 | x |
| | 10 | 11.0 | O | 15.1 | O | 24.5 | x |
| Amylose (control) | 0 | 7.1 | ◎ | 13.2 | ◎ | 21.6 | Δ |
| | 5 | 7.3 | ◎ | 13.7 | ◎ | 22.3 | Δ |

TABLE 1-continued

| Film material | Glycerine added(%) | RH 33% water content | properties | RH 65% water content | properties | RH 90% water content | properties |
|---|---|---|---|---|---|---|---|
| | 10 | 7.8 | ◉ | 14.3 | ◉ | 23.5 | Δ |

Notes:
O: transparent, glossy, and tough. no blocking
x: transparent, glossy, soft, and low in tensile strength. blocking
◉: transparent, glossy, brittle, and low in folding endurance. no blocking
Δ: opaque, unglossy, brittle, and low in folding endurance. no blocking As is clear from Table 1, the elsinan films of the invention are desirably transparent, glossy, tough and flexible.

The properties are independent of RH, unchangeable during storage, and are superior to those of pullulan or amylose films.

The tensile strength, folding endurance, oxygen permeability, and heat-sealability were tested with films free of glycerin under the condition of RH 65%.

The results are shown in Table 2.

TABLE 2

| Film material | Tensile strength (kg/cm$^2$) | Folding endurance (times) | Oxygen permeability (cc/cm$^2$ . 24 hr. atm) | Heat-sealability |
|---|---|---|---|---|
| Elsinan (the product of the invention) | 950 | 973 | 1.0 | +++ |
| Pullulan (control) | 830 | 742 | 1.3 | + |
| Amylose (control) | 420 | 94 | 1.5 | − |

Notes:
+++: firmly heat-sealable
+: normally heat-sealable
−: unheat-sealable

As is clear from Table 2, it can be seen that elsinan film has the most excellent tensile strength, folding endurance, and toughness and flexibility. Since elsinan film is highly oxygen impermeable, and is heat-sealable, it is effective to coat or seal articles liable to oxidation, and elsinan film can prolong the storage period and effective period of the contents that required protection against atmospheric oxygen.

EXAMPLE 2

Film

A 10 w/w % aqueous elsinan solution containing 0.2 w/w % sucrose monolaurate based on elsinan, d.s.b., was prepared and cast on metal rolls plated with chrome which were heated to 60° C. to prepare a film of 0.03 mm in thickness at the take-up speed of 3 m/min.

The film was also excellent similarly as in the case of Example 1, being high in oxygen impermeability, transparent, glossy, tough and flexible.

EXAMPLE 3

Film

A 7 w/w % aqueous elsinan solution containing 10 w/w % polyvinyl alcohol and 1 w/w % maltitol based on elsinan, d.s.b., was prepared and applied on a metal plate and dried with hot air at 80° C.

The obtained film was excellent similarly as in the case of Example 1, being high oxygen impermeable, transparent, glossy, tough and flexible.

EXAMPLE 4

Fiber

A spinning solution at 60° C. containing 40 w/w % elsinan was extruded through a cylindrical nozzle of 0.3 mm in diameter and 1 mm in length under a pressure of 3 kg/cm$^2$ into air at room temperature, and the obtained strand from the nozzle was wound up by a winding machine while evaporating the moisture from the strand with air.

The filaments of the strand were about 20 microns in diameter, and tough and flexible. The filaments can be twined, knitted, and weaved freely.

Since the filament is characterized in that they are hydrophylic, non-toxic and non-irritative to the skin, they are suitable for the production of medicinal or sanitary goods, e.g., absorbent cotton, women's sanitary cotton, gauze, and suture.

The fibers blended or combined with elsinan filaments and others still have the properties of elsinan i.e., moisture absorption, non-electric chargeable and dyeability and can be used for preparing underwear or other clothing materials.

EXAMPLE 5

Paper

A mixture comprising 1 part of elsinan fibers obtained by Example 4, cut to a length of 5 to 10 cm, and about one half part of wood pulp was prepared and suspended uniformly in water at 10° C. of about 50 times of the amount by weight of the mixture. The resulting suspension was subjected to a paper machine, a drying roll at 50° to 80° C. and a calender roll to prepare a sheet of paper.

The paper has a smooth but less glossy surface and is similar in texture to Japanese paper. The paper has a favorable writing ink receptivity, and is not blurred by ink.

Since the paper is readily soluble in hot water, it is suitable for special uses such as for secret documents. Since the paper is edible, it is usable preferably as internal packaging materials for medicines and powdered foods such as condiment, instant coffee and cocoa.

EXAMPLE 6

Coating

Fresh eggs within 10 hours after laying were dipped in a 1.0 w/w % aqueous elsinan solution at 30° C. for 30 seconds, and then the resulting eggs were dried with warm air at 30° C. for 2 hours to provide elsinan coating on the eggs.

The obtained coated eggs were kept at room temperature (15° to 25° C.) and the edible period of the eggs was compared with those of uncoated eggs used as controls. As a result, the coated eggs had an edible period of about 5 to 10 times longer than the uncoated eggs.

A citrus fruit (Sudachi, *Citrus sudachi*) coated with elsinan in the same manner as described above was superior to the uncoated fruit in maintaining its original freshness, greeness and fragrance about 5 to 10 times longer than the uncoated fruit.

EXAMPLE 7

Packaging materials for extraction

Commercially available small bags for black tea, made of a coarse filter paper, were coated on both sides or on one side with a 5 w/w % aqueous elsinan solution containing 50 w/w % pullulan based on elsinan, d.s.b., by calendering and drying with hot air at 60° C.

One serving of black tea was packed in the obtained small bags. Commercially available small bags containing black tea of the same quality were used as controls. These small bags were allowed to stand for a month under the condition of RH 60% and a temperature of 30° C. Hot black tea prepared by pouring boiling water on the bags was tested on aroma, color and palatability.

When boiling water was poured on the bags coated with the elsinan of the invention, the contents in elsinan coated bags could be extracted equally easily as the controls. Both extracts were transparent, but the extracts prepared with elsinan coated bags were superior in aroma, color, and palatability to the extracts of the uncoated bags.

EXAMPLE 8

Cup

Water was sprayed on elsinan while stirring to bring its water content to about 30 w/w %. Strands were prepared with the resulting elsinan using an extruder and cut into pellets of 2.5 mm in diameter and 4 mm in length. Cups were formed from the pellets using an injection molding machine at a temperature of 120° C.

The obtained cups are desirably tough and transparent.

EXAMPLE 9

Foamed sheet

One hundred parts by weight of polyvinyl chloride resin were mixed with 60 parts by weight of dioctylphthalate, a plasticizer, and to the mixture was admixed 30 w/w % of elsinan containing 50 w/w % water. The resulting mixture was kneaded thoroughly with a kneader to form a homogeneous plastisol which was then cast on an aluminum plate with an applicator to prepare a sheet having a thickness of 3 mm. The sheet was heat-treated for 10 minutes in an oven kept at 190° C. to obtain a sheet having a foamed ratio of about 5 times of the original volume and having uniform cells.

The product is desirable for soundproofing materials, heat insulation materials, packaging materials, and shock absorbing materials. The product decomposed within a month when exposed to river water, but a sheet to which elsinan was not added maintained its original shape even after 12 months.

EXAMPLE 10

Fertilizer pellet

The compound fertilizer (N=14%, $P_2O_5$=8%, $K_2O$=12%), elsinan, calcium, and water were mixed sufficiently at the ratio of 70:10:15:5 by weight. The resulting mixture was subjected to an extruder (L/D=20, compression ratio=1.8, inner diameter of die orifice=30 mm) with heating to 80° C. to produce fertilizer pellets.

The fertilizer can be produced without necessitating the use of a fertilizer container, so it is easy to handle. The fertilizer has a sufficient mechanical strength for deep placement, and permits controlled release of the ingredients of fertilizer by changing the mixing ratio. If necessary, botanical hormone, agricultural medicine, and soil conditioner can be easily incorporated into the fertilizer pile.

EXAMPLE 11

Shaped matters of tobacco

Fifty parts by weight of a starting tobacco powder of the yellow grade and 200 parts by weight of a 2 w/w % aqueous elsinan solution were mixed with 0.1 parts by weight of maltitol. The resulting mixture was extruded through a 0.2 mm slit onto a stainless-steel endless belt, and then dried with infrared rays to obtain 65 parts by weight of a sheet tobacco having a water content of 13 w/w %. The product is preferable not only as blend of leaf tobacco for cigarettes but also as bunching and wrapping materials for cigars and cigarrillos.

The product retains the desirable inherent aroma of tobacco and does not generate offensive taste and odor. The products inhibit deterioration of the various tobacco contents therein. When the product is smoked, it is satisfactory in aroma and flavor. The nicotine content or combustion speed of the product can be controlled by changing the mixing ratio of elsinan.

EXAMPLE 12

Tablet

To 100 g of a 40 w/w % aqueous elsinan solution with a temperature of 80° C. was added 140 g maltose and 20 g (1,000,000 I.U./g) vitamin A palmitate and then mixed sufficiently. The resulting mixture was cast on a glass plate, dried with aeration and pulverized. Tablets were made with the pulverized product with a tableting machine.

The tablets contained 100,000 I.U. per gram of vitamin A palmitate. The vitamin A palmitate content in the tablet is difficultly decomposable by oxidation; hardly decomposed after 3 months storage at 30° C.

EXAMPLE 13

Capsule

A 15 w/w % aqueous elsinan solution was warmed to 60° C. and deaerated. Then, capsule shaping metal rods were dipped in the solution, taken out promptly and dried gradually with warm air at 40° C. The obtained capsules were very elastic, glossy, transparent and excellent "hard" capsules free of deformation.

When the capsules are used as containers for oral medicines, they are preferable containers that decompose in the intestine because they are decomposed only by intestinal amylase but hardly decomposable in the stomach.

EXAMPLE 14

Adhesive

A mixture of 30 parts by weight of dimethyl sulfoxide, 25 parts by weight of water, 5 parts by weight of elsinan, 5 parts by weight of pullulan and 2 parts by weight of dibenzylidenexylite was stirred at 90° C. for one hour until it gave a homogeneous solution. Thereafter the solution was poured into a cylindrical container, equipped with a screw up-screw down device similar to that in lipstick containers and having a diameter of 14 mm and a height of 50 mm, and allowed to cool at room temperature to provide a solid adhesive.

When the solid adhesive was applied on kraft paper, it could be applied on with an excellent spreadability to form a uniform thin layer because it had no excessive stringiness.

The adhesive keeps its appropriate solidity and hardness over a wide temperature range and after prolonged storage, and could be always used successfully, exhibiting prolongly its initial strengths and properties.

EXAMPLE 15

Tube

Powder elsinan was mixed with 40 w/w % glycerin per elsinan, and the resulting mixture was kneaded with heating to prepare a homogeneous melt. The melt was subjected to an extruder at 120° and 150° C. to form a tube of 8 mm in inner diameter and 1 mm in thickness. The product was transparent and high in elasticity.

EXAMPLE 16

Sponge

Powder elsinan was mixed with 30 w/w % water and 35 w/w % glycerin per elsinan. The resulting mixture was thoroughly kneaded with a kneader. Subsequently the mixture was subjected to an applicator and on an aluminum plate was formed a sheet of 3 mm in thickness. The resulting sheet was heated for 10 minutes in an oven kept at 190° C. to obtain a sponge having uniform cells.

The product is suitable for various materials such as soundproofing materials, heat insulation materials, packaging materials, shock absorbing materials, water absorbing materials, water holding materials, and toy materials.

What we claim is:

1. A shaped body consisting essentially of an alpha-glucan having a molecular weight of about 10,000 to about 10,000,000 comprising repeating units of [3)-Glc-(1→4)-Glc-(1→4)-Glc-(1→], wherein Glc represents an alpha-D-glucopyranose residue.

2. A product in accordance with claim 1 wherein said shaped body is composed of said alpha-glucan alone.

3. A product in accordance with claim 1 wherein the shaped body is in the form of a tube.

4. A product in accordance with claim 1, wherein said shaped body is composed of said alpha-glucan in combination with a plasticizer or filler.